US005688691A

United States Patent [19]
Oro et al.

[11] Patent Number: 5,688,691
[45] Date of Patent: Nov. 18, 1997

[54] INSECT RETINOID-LIKE RECEPTOR COMPOSITIONS AND METHODS

[75] Inventors: Anthony E. Oro, San Diego; Ronald M. Evans, La Jolla, both of Calif.

[73] Assignee: The Salk Institute for Biological Studies, La Jolla, Calif.

[21] Appl. No.: 464,272

[22] Filed: Jun. 5, 1995

Related U.S. Application Data

[63] Continuation of Ser. No. 13,975, Feb. 4, 1993, abandoned, which is a continuation-in-part of Ser. No. 497,935, Mar. 22, 1990, abandoned.

[51] Int. Cl.$^6$ .............. C12N 1/20; C12N 15/00; C07H 21/04

[52] U.S. Cl. .............. 455/348; 435/69.1; 435/325; 435/252.3; 435/320.1; 536/23.5; 536/24.31; 935/9; 935/10; 935/11; 935/22; 935/88

[58] Field of Search .................. 536/23.5, 24.31; 435/320.1, 240.26, 69.1, 252.3, 325, 348; 935/1, 66, 70, 76, 9, 10, 11, 22, 88; 530/350

[56] References Cited

PUBLICATIONS

Oro, et al., *Nature*, vol. 347, 20 Sep. 1990, pp. 298–301.
Sequence Comparison, Citing Oro, et al., *Nature*, vol. 347, 20 Sep. 1990, 298–301.
Boehringer Mannheim Biochemicals, Reagents for Molecular Biology, p. 261, 1990.

*Primary Examiner*—Bradley L. Sisson
*Attorney, Agent, or Firm*—Gray Cary Ware & Freidenrich; Stephen E. Reiter

[57] ABSTRACT

The present invention relates to the discovery of novel insect receptor polypeptides, which, when complexed with certain ligands, or otherwise activated by certain compounds, modulate transcription of certain genes by binding to cognate response elements associated with the promoters of the genes. The novel receptors of the invention are substantially similar to previously discovered mammalian receptors which are activated to modulate transcription of certain genes in cells, when the cells are exposed to retinoic acid. The invention provides DNAs encoding the novel receptors, including expression vectors for expression of the receptors in cells; cells transformed with such expression vectors; cells co-transformed with such expression vectors and with reporter vectors to monitor activation of the receptors to modulate transcription, when the cells are exposed to ligand for the invention receptor; and methods of using such co-transformed cells in screening for compounds which are capable of leading to activation of the receptors and for compounds which are capable of interfering with such activation and, as such, are potentially potent insecticides. The invention also provides DNA and RNA probes for identifying DNA's encoding related receptors, of insects and other animals, of the class, to which the novel receptors of the invention belong.

13 Claims, 1 Drawing Sheet

FIG. 1

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2304 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 163..1704

( x i ) SEQUENCE DESCRIPTION: SEQ ID NO:1:

```
GGACACGGTG  GCGTTGGCAA  AGTGAAACCC  CAACAGAGAG  GCGAAAGCGA  GCCAAGACAC         60

ACCACATACA  CACGAAGAGA  ACGAGCAAGA  AGAAACCGGT  AGGCGGAGGA  GGCGCTGCCC        120

CCAGTTCCTC  CAATATACCC  AGCACCACAT  CACAAGCCCA  GG ATG GAC AAC TGC            174
                                                  Met Asp Asn Cys
                                                   1

GAC CAG GAC GCC AGC TTT CGG CTG AGC CAC ATC AAG GAG GAG GTC AAG              222
Asp Gln Asp Ala Ser Phe Arg Leu Ser His Ile Lys Glu Glu Val Lys
  5              10                  15                  20

CCG GAC ATC TCG CAG CTG AAC GAC AGC AAC AAC AGC AGC TTT TCG CCC              270
Pro Asp Ile Ser Gln Leu Asn Asp Ser Asn Asn Ser Ser Phe Ser Pro
             25                  30                  35

AAG GCC GAG AGT CCC GTG CCC TTC ATG CAG GCC ATG TCC ATG GTC CAC              318
Lys Ala Glu Ser Pro Val Pro Phe Met Gln Ala Met Ser Met Val His
         40                  45                  50

GTG CTG CCC GGC TCC AAC TCC GCC AGC TCC AAC AAC AAC AGC GCT GGA              366
Val Leu Pro Gly Ser Asn Ser Ala Ser Ser Asn Asn Asn Ser Ala Gly
         55                  60                  65

GAT GCC CAA ATG GCG CAG GCG CCC AAT TCG GCT GGA GGC TCT GCC GCC              414
Asp Ala Gln Met Ala Gln Ala Pro Asn Ser Ala Gly Gly Ser Ala Ala
         70                  75                  80

GCT GCA GTC CAG CAG CAG TAT CCG CCT AAC CAT CCG CTG AGC GGC AGC              462
Ala Ala Val Gln Gln Gln Tyr Pro Pro Asn His Pro Leu Ser Gly Ser
 85                  90                  95                 100

AAG CAC CTC TGC TCT ATT TGC GGG GAT CGG GCC AGT GGC AAG CAC TAC              510
Lys His Leu Cys Ser Ile Cys Gly Asp Arg Ala Ser Gly Lys His Tyr
                105                 110                 115

GGC GTG TAC AGC TGT GAG GGC TGC AAG GGC TTC TTT AAA CGC ACA GTG              558
Gly Val Tyr Ser Cys Glu Gly Cys Lys Gly Phe Phe Lys Arg Thr Val
                120                 125                 130

CGC AAG GAT CTC ACA TAC GCT TGC AGG GAG AAC CGC AAC TGC ATC ATA              606
Arg Lys Asp Leu Thr Tyr Ala Cys Arg Glu Asn Arg Asn Cys Ile Ile
            135                 140                 145

GAC AAG CGG CAG AGG AAC CGC TGC CAG TAC TGC CGC TAC CAG AAG TGC              654
Asp Lys Arg Gln Arg Asn Arg Cys Gln Tyr Cys Arg Tyr Gln Lys Cys
        150                 155                 160
```

-continued

| | | | | | | | | | | | | | | | | |
|---|---|---|---|---|---|---|---|---|---|---|---|---|---|---|---|---|
| CTA | ACC | TGC | GGC | ATG | AAG | CGC | GAA | GCG | GTC | CAG | GAG | GAG | CGT | CAA | CGC | 702 |
| Leu | Thr | Cys | Gly | Met | Lys | Arg | Glu | Ala | Val | Gln | Glu | Glu | Arg | Gln | Arg | |
| 165 | | | | 170 | | | | | 175 | | | | | | 180 | |
| GGC | GCC | CGC | AAT | GCG | GCG | GGT | AGG | CTC | AGC | GCC | AGC | GGA | GGC | GGC | AGT | 750 |
| Gly | Ala | Arg | Asn | Ala | Ala | Gly | Arg | Leu | Ser | Ala | Ser | Gly | Gly | Gly | Ser | |
| | | | | 185 | | | | | 190 | | | | | 195 | | |
| AGC | GGT | CCA | GGT | TCG | GTA | GGC | GGA | TCC | AGC | TCT | CAA | GGC | GGA | GGA | GGA | 798 |
| Ser | Gly | Pro | Gly | Ser | Val | Gly | Gly | Ser | Ser | Ser | Gln | Gly | Gly | Gly | Gly | |
| | | | 200 | | | | | 205 | | | | | 210 | | | |
| GGA | GGC | GGC | GTT | TCT | GGC | GGA | ATG | GGC | AGC | GGC | AAC | GGT | TCT | GAT | GAC | 846 |
| Gly | Gly | Gly | Val | Ser | Gly | Gly | Met | Gly | Ser | Gly | Asn | Gly | Ser | Asp | Asp | |
| | | 215 | | | | | 220 | | | | | 225 | | | | |
| TTC | ATG | ACC | AAT | AGC | GTG | TCC | AGG | GAT | TTC | TCG | ATC | GAG | CGC | ATC | ATA | 894 |
| Phe | Met | Thr | Asn | Ser | Val | Ser | Arg | Asp | Phe | Ser | Ile | Glu | Arg | Ile | Ile | |
| | 230 | | | | 235 | | | | | 240 | | | | | | |
| GAG | GCC | GAG | CAG | CGA | GCG | GAG | ACC | CAA | TGC | GGC | GAT | CGT | GCA | CTG | ACG | 942 |
| Glu | Ala | Glu | Gln | Arg | Ala | Glu | Thr | Gln | Cys | Gly | Asp | Arg | Ala | Leu | Thr | |
| 245 | | | | | 250 | | | | | 255 | | | | | 260 | |
| TTC | CTG | CGC | GTT | GGT | CCC | TAT | TCC | ACA | GTC | CAG | CCG | GAC | TAC | AAG | GGT | 990 |
| Phe | Leu | Arg | Val | Gly | Pro | Tyr | Ser | Thr | Val | Gln | Pro | Asp | Tyr | Lys | Gly | |
| | | | | 265 | | | | | 270 | | | | | 275 | | |
| GCC | GTG | TCG | GCC | CTG | TGC | CAA | GTG | GTC | AAC | AAA | CAG | CTC | TTC | CAG | ATG | 1038 |
| Ala | Val | Ser | Ala | Leu | Cys | Gln | Val | Val | Asn | Lys | Gln | Leu | Phe | Gln | Met | |
| | | | 280 | | | | | 285 | | | | | 290 | | | |
| GTC | GAA | TAC | GCG | CGC | ATG | ATG | CCG | CAC | TTT | GCC | CAG | GTG | CCG | CTG | GAC | 1086 |
| Val | Glu | Tyr | Ala | Arg | Met | Met | Pro | His | Phe | Ala | Gln | Val | Pro | Leu | Asp | |
| | | 295 | | | | | 300 | | | | | 305 | | | | |
| GAC | CAG | GTG | ATT | CTG | CTG | AAA | GCC | GCT | TGG | ATC | GAG | CTG | CTC | ATT | GCG | 1134 |
| Asp | Gln | Val | Ile | Leu | Leu | Lys | Ala | Ala | Trp | Ile | Glu | Leu | Leu | Ile | Ala | |
| | 310 | | | | 315 | | | | | 320 | | | | | | |
| AAC | GTG | GCC | TGG | TGC | AGC | ATC | GTT | TCG | CTG | GAT | GAC | GGC | GGT | GCC | GGC | 1182 |
| Asn | Val | Ala | Trp | Cys | Ser | Ile | Val | Ser | Leu | Asp | Asp | Gly | Gly | Ala | Gly | |
| 325 | | | | | 330 | | | | | 335 | | | | | 340 | |
| GGC | GGG | GGC | GGT | GGA | CTA | GGC | CAC | GAT | GGC | TCC | TTT | GAG | CGA | CGA | TCA | 1230 |
| Gly | Gly | Gly | Gly | Gly | Leu | Gly | His | Asp | Gly | Ser | Phe | Glu | Arg | Arg | Ser | |
| | | | | 345 | | | | | 350 | | | | | 355 | | |
| CCG | GGC | CTT | CAG | CCC | CAG | CAG | CTG | TTC | CTC | AAC | CAG | AGC | TTC | TCG | TAC | 1278 |
| Pro | Gly | Leu | Gln | Pro | Gln | Gln | Leu | Phe | Leu | Asn | Gln | Ser | Phe | Ser | Tyr | |
| | | | 360 | | | | | 365 | | | | | 370 | | | |
| CAT | CGC | AAC | AGT | GCG | ATC | AAA | GCC | GGT | GTG | TCA | GCC | ATC | TTC | GAC | CGC | 1326 |
| His | Arg | Asn | Ser | Ala | Ile | Lys | Ala | Gly | Val | Ser | Ala | Ile | Phe | Asp | Arg | |
| | | | 375 | | | | | 380 | | | | | 385 | | | |
| ATA | TTG | TCG | GAG | CTG | AGT | GTA | AAG | ATG | AAG | CGG | CTG | AAT | CTC | GAC | CGA | 1374 |
| Ile | Leu | Ser | Glu | Leu | Ser | Val | Lys | Met | Lys | Arg | Leu | Asn | Leu | Asp | Arg | |
| | | | 390 | | | | 395 | | | | | 400 | | | | |
| CGC | GAG | CTG | TCC | TGC | TTG | AAG | GCC | ATC | ATA | CTG | TAC | AAC | CCG | GAC | ATA | 1422 |
| Arg | Glu | Leu | Ser | Cys | Leu | Lys | Ala | Ile | Ile | Leu | Tyr | Asn | Pro | Asp | Ile | |
| 405 | | | | | 410 | | | | | 415 | | | | | 420 | |
| CGC | GGG | ATC | AAG | AGC | CGG | GCG | GAG | ATC | GAG | ATG | TGC | CGC | GAG | AAG | GTG | 1470 |
| Arg | Gly | Ile | Lys | Ser | Arg | Ala | Glu | Ile | Glu | Met | Cys | Arg | Glu | Lys | Val | |
| | | | | 425 | | | | | 430 | | | | | 435 | | |
| TAC | GCT | TGC | CTG | GAC | GAG | CAC | TGC | CGC | CTG | GAA | CAT | CCG | GGC | GAC | GAT | 1518 |
| Tyr | Ala | Cys | Leu | Asp | Glu | His | Cys | Arg | Leu | Glu | His | Pro | Gly | Asp | Asp | |
| | | | 440 | | | | 445 | | | | | 450 | | | | |
| GGA | CGC | TTT | GCG | CAA | CTG | CTG | CTG | CGT | CTG | CGC | CGC | TTT | GCG | ATC | GAT | 1566 |
| Gly | Arg | Phe | Ala | Gln | Leu | Leu | Leu | Arg | Leu | Arg | Arg | Phe | Ala | Ile | Asp | |
| | | 455 | | | | | 460 | | | | | 465 | | | | |
| CAG | CCT | GAA | GTG | CCA | GGA | TCA | CCT | GTT | CCT | CTT | CCG | CAT | TAC | CAG | CGA | 1614 |
| Gln | Pro | Glu | Val | Pro | Gly | Ser | Pro | Val | Pro | Leu | Pro | His | Tyr | Gln | Arg | |
| 470 | | | | | 475 | | | | | 480 | | | | | | |

-continued

| | | | | | | | | | | | | | | | |
|---|---|---|---|---|---|---|---|---|---|---|---|---|---|---|---|
| CCG | GCC | GCT | GGA | GGA | GCT | CTT | TCT | CGA | GCA | GCT | GGA | GGC | GCC | GCC | GCC |
| Pro | Ala | Ala | Gly | Gly | Ala | Leu | Ser | Arg | Ala | Ala | Gly | Gly | Ala | Ala | Ala |
| 485 | | | | 490 | | | | | 495 | | | | | 500 | |

1662

| | | | | | | | | | |
|---|---|---|---|---|---|---|---|---|---|
| ACC | CGG | CCT | GGC | GAT | GAA | ACT | GGA | GTA | GGG | TCC | CGA | CTC | TAAAGTCGCC |
| Thr | Arg | Pro | Gly | Asp | Glu | Thr | Gly | Val | Gly | Ser | Arg | Leu | |
| | | | | 505 | | | | | 510 | | | | |

1711

```
CCCGTTCTCC ATCCGAAAAA TGTTTCATTG TGATTGCGTT TGTTTGCATT TCTCCTCTCT    1771
ATCCCTACAA AAGCCCCCTA ATATTACGCA AATGTGTAT  GTAATTGTTT ATTTTTTTT     1831
TATTACCTAA TATTATTATT ATTATTGATA TAGAAAATGT TTTCCTTAAG ATGAAGATTA    1891
GCCTCCTCGA CGTTTATGTC CCAGTAAACG AAAAACAAAC AAAATCCAAA ACTTGAAAAG    1951
AACACAAAAC ACGAACGAGA AAATGCACAC AAGCAAAGTA AAGTAAAAG  TTAAACTAAA    2011
GCTAAACGAG TAAAGATATT AAAATAACGG TTAAAATTAA TGCATAGTTA TGATCTACAG    2071
ACGTATGTAA ACATACAAAT TCAGCATAAA TATATATGTC AGCAGGCGCA TATCTGCGGT    2131
GCTGGCCCCG TTCTAAACCA ATTGTAATTA CTTTTTAACA TAAATTTACC CAAAACGTTA    2191
TCAATTAGAT GCGAGATACA AAAATCACCG ACGAAAACCA ACAAAATATA TCTATGTATA    2251
AAAATATAA  GCTGCATAAC AAAAAAAAAA AAAAAAAAAA AAAAAAAAA  AAA           2304
```

( 2 ) INFORMATION FOR SEQ ID NO:2:

( i ) SEQUENCE CHARACTERISTICS:
        ( A ) LENGTH: 513 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Asp Asn Cys Asp Gln Asp Ala Ser Phe Arg Leu Ser His Ile Lys
 1           5                  10                  15

Glu Glu Val Lys Pro Asp Ile Ser Gln Leu Asn Asp Ser Asn Asn Ser
            20                  25                  30

Ser Phe Ser Pro Lys Ala Glu Ser Pro Val Pro Phe Met Gln Ala Met
        35                  40                  45

Ser Met Val His Val Leu Pro Gly Ser Asn Ser Ala Ser Ser Asn Asn
    50                  55                  60

Asn Ser Ala Gly Asp Ala Gln Met Ala Gln Ala Pro Asn Ser Ala Gly
65                  70                  75                  80

Gly Ser Ala Ala Ala Ala Val Gln Gln Gln Tyr Pro Pro Asn His Pro
                85                  90                  95

Leu Ser Gly Ser Lys His Leu Cys Ser Ile Cys Gly Asp Arg Ala Ser
            100                 105                 110

Gly Lys His Tyr Gly Val Tyr Ser Cys Glu Gly Cys Lys Gly Phe Phe
        115                 120                 125

Lys Arg Thr Val Arg Lys Asp Leu Thr Tyr Ala Cys Arg Glu Asn Arg
    130                 135                 140

Asn Cys Ile Ile Asp Lys Arg Gln Arg Asn Arg Cys Gln Tyr Cys Arg
145                 150                 155                 160

Tyr Gln Lys Cys Leu Thr Cys Gly Met Lys Arg Glu Ala Val Gln Glu
                165                 170                 175

Glu Arg Gln Arg Gly Ala Arg Asn Ala Ala Gly Arg Leu Ser Ala Ser
            180                 185                 190

Gly Gly Gly Ser Ser Gly Pro Gly Ser Val Gly Ser Ser Ser Gln
        195                 200                 205

Gly Gly Gly Gly Gly Gly Gly Val Ser Gly Gly Met Gly Ser Gly Asn
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     |     |     | 210 |     |     |     |     | 215 |     |     |     |     | 220 |
| Gly | Ser | Asp | Asp | Phe | Met | Thr | Asn | Ser | Val | Ser | Arg | Asp | Phe | Ser | Ile |
| 225 |     |     |     |     | 230 |     |     |     |     | 235 |     |     |     |     | 240 |
| Glu | Arg | Ile | Ile | Glu | Ala | Glu | Gln | Arg | Ala | Glu | Thr | Gln | Cys | Gly | Asp |
|     |     |     |     | 245 |     |     |     |     | 250 |     |     |     |     | 255 |     |
| Arg | Ala | Leu | Thr | Phe | Leu | Arg | Val | Gly | Pro | Tyr | Ser | Thr | Val | Gln | Pro |
|     |     |     | 260 |     |     |     |     | 265 |     |     |     |     | 270 |     |     |
| Asp | Tyr | Lys | Gly | Ala | Val | Ser | Ala | Leu | Cys | Gln | Val | Val | Asn | Lys | Gln |
|     |     | 275 |     |     |     |     | 280 |     |     |     |     | 285 |     |     |     |
| Leu | Phe | Gln | Met | Val | Glu | Tyr | Ala | Arg | Met | Met | Pro | His | Phe | Ala | Gln |
|     | 290 |     |     |     |     | 295 |     |     |     |     | 300 |     |     |     |     |
| Val | Pro | Leu | Asp | Asp | Gln | Val | Ile | Leu | Leu | Lys | Ala | Ala | Trp | Ile | Glu |
| 305 |     |     |     |     | 310 |     |     |     |     | 315 |     |     |     |     | 320 |
| Leu | Leu | Ile | Ala | Asn | Val | Ala | Trp | Cys | Ser | Ile | Val | Ser | Leu | Asp | Asp |
|     |     |     |     | 325 |     |     |     |     | 330 |     |     |     |     | 335 |     |
| Gly | Gly | Ala | Gly | Gly | Gly | Gly | Gly | Leu | Gly | His | Asp | Gly | Ser | Phe |     |
|     |     |     | 340 |     |     |     |     | 345 |     |     |     |     | 350 |     |     |
| Glu | Arg | Arg | Ser | Pro | Gly | Leu | Gln | Pro | Gln | Gln | Leu | Phe | Leu | Asn | Gln |
|     |     | 355 |     |     |     |     | 360 |     |     |     |     | 365 |     |     |     |
| Ser | Phe | Ser | Tyr | His | Arg | Asn | Ser | Ala | Ile | Lys | Ala | Gly | Val | Ser | Ala |
|     | 370 |     |     |     |     | 375 |     |     |     |     | 380 |     |     |     |     |
| Ile | Phe | Asp | Arg | Ile | Leu | Ser | Glu | Leu | Ser | Val | Lys | Met | Lys | Arg | Leu |
| 385 |     |     |     |     | 390 |     |     |     |     | 395 |     |     |     |     | 400 |
| Asn | Leu | Asp | Arg | Arg | Glu | Leu | Ser | Cys | Leu | Lys | Ala | Ile | Ile | Leu | Tyr |
|     |     |     |     | 405 |     |     |     |     | 410 |     |     |     |     | 415 |     |
| Asn | Pro | Asp | Ile | Arg | Gly | Ile | Lys | Ser | Arg | Ala | Glu | Ile | Glu | Met | Cys |
|     |     |     | 420 |     |     |     |     | 425 |     |     |     |     | 430 |     |     |
| Arg | Glu | Lys | Val | Tyr | Ala | Cys | Leu | Asp | Glu | His | Cys | Arg | Leu | Glu | His |
|     |     | 435 |     |     |     |     | 440 |     |     |     |     | 445 |     |     |     |
| Pro | Gly | Asp | Asp | Gly | Arg | Phe | Ala | Gln | Leu | Leu | Leu | Arg | Leu | Arg | Arg |
|     | 450 |     |     |     |     | 455 |     |     |     |     | 460 |     |     |     |     |
| Phe | Ala | Ile | Asp | Gln | Pro | Glu | Val | Pro | Gly | Ser | Pro | Val | Pro | Leu | Pro |
| 465 |     |     |     |     | 470 |     |     |     |     | 475 |     |     |     |     | 480 |
| His | Tyr | Gln | Arg | Pro | Ala | Ala | Gly | Gly | Ala | Leu | Ser | Arg | Ala | Ala | Gly |
|     |     |     |     | 485 |     |     |     |     | 490 |     |     |     |     | 495 |     |
| Gly | Ala | Ala | Ala | Thr | Arg | Pro | Gly | Asp | Glu | Thr | Gly | Val | Gly | Ser | Arg |
|     |     |     | 500 |     |     |     |     | 505 |     |     |     |     | 510 |     |     |
| Leu |     |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: both     ( i i ) MOLECULE TYPE: DNA (genomic)

( x i ) SEQUENCE DESCRIPTION: SEQ ID NO:3:

GATCCGATAT CCATATGGAA TTCGGTACCA    30

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: both -continued (D) TOPOLOGY: both (i i) MOLECULE TYPE: DNA (genomic)

(x i) SEQUENCE DESCRIPTION: SEQ ID NO:4:

AGGTCATGAC CT                                                                                         1 2

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: both
        (D) TOPOLOGY: both     (i i) MOLECULE TYPE: DNA (genomic)

(x i) SEQUENCE DESCRIPTION: SEQ ID NO:5:

CTAGAGGTCA TGACCT                                                                                     1 6

INSECT RETINOID-LIKE RECEPTOR COMPOSITIONS AND METHODS

This application is a file-wrapper continuation of application Ser. No. 08/013,975, filed Feb. 4, 1993, now abandoned, which is a continuation-in-part of United States Application Ser. No. 07/497,935, filed Mar. 22, 1990, now abandoned, the entire contents of which are hereby incorporated by reference herein.

The present invention concerns novel, steroid-hormone-receptor-like proteins, DNA encoding same, cells transfected with said DNA and methods of making and using same. More particularly, the invention relates to proteins that occur in insects. Invention proteins have a substantial degree of similarity with respect to mammalian receptors which have transcription-modulating effects, at affected promoters, and which are responsive to the presence of retinoic acid and other retinoids, as well as vitamin A metabolites.

BACKGROUND OF THE INVENTION

Retinoids comprise a group of compounds including retinoic acid, retinol (vitamin A), retinal, retinyl acetate, retinyl palmitate, and natural and synthetic derivatives of these compounds, that together exert a profound effect on development and differentiation in a wide variety of systems. Although early studies focused on the effect of retinoids on growth and differentiation of epithelial cells, their actions have been shown to be widespread. Recent studies have examined the effects of retinoids on a variety of cultured neoplastic cell types, including the human promyelocytic leukemia cell line, HL60, where retinoic acid appears to be a potent inducer of granulocyte differentiation. In F9 embryonal carcinoma cells, retinoic acid will induce the differentiation of parietal endoderm, characteristic of a late mouse blastocyst. Retinoic acid also appears to play an important role in defining spatial-temporal axes in the developing avian limb and the regenerating amphibian limb.

Retinoic acid has been shown to induce the transcription of several cDNAs that have been isolated by differential screening, supporting the hypothesis that retinoic acid exerts its action via modulation of gene expression, mediated by a receptor protein.

The ability to identify compounds able to affect transcription of insect genes could be of significant value, as such compounds may be useful as insecticides. Of significance in this regard would be the identification of receptor proteins which modulate transcription of insect genes.

Through molecular cloning studies it has been possible to demonstrate that mammalian receptors for steroid, retinoid and thyroid hormones are all structurally related and comprise a superfamily of regulatory proteins that are capable of modulating specific gene expression in response to exposure to hormone, by binding directly to cis-acting elements [see, for example, Evans, Science 240:889 (1988); and Green and Chambon, Trends Genet. 4:309 (1988)]. Structural comparisons and functional studies with mutant receptors have made it possible to discern that these molecules are composed of a series of discrete functional domains, most notably, a DNA-binding domain that is composed typically of 66–68 amino acids, including two zinc fingers, and an associated carboxy terminal stretch of approximately 250 amino acids which comprises the ligand-binding domain (reviewed in Evans, supra).

An important advance in the characterization of this superfamily has been the delineation of a growing list of polypeptides encoded by DNA which has been isolated by low-stringency hybridization techniques using known receptor probes. These polypeptides possess the structural features of hormone receptors.

A retinoic acid dependent transcription factor, referred to as RAR-alpha (retinoic acid receptor-alpha), has been identified. Subsequently, two additional RAR-related genes were isolated, and there are now at least three different RAR subtypes (alpha, beta and gamma) known to exist in mice and humans. These retinoic acid receptors (RARs) share homology with steroid hormone and thyroid hormone receptors and have been shown to regulate specific gene expression by a similar, ligand-dependent mechanism (Umesono et al., Nature 336:262 (1988)). These RAR subtypes are expressed in distinct patterns throughout development and in the mature organism.

Recently, another retinoic acid-dependent transcription factor, designated RXR-alpha, has been identified in cDNA libraries prepared from human cells. RXR-alpha differs significantly in primary amino acid sequence from human RAR-alpha and other known members of the mammalian steroid/thyroid hormone superfamily of receptors; but, like other members of the superfamily, RXR-alpha is activated to effect transcription trans-activation in mammalian and insect cells exposed to retinoic acid and retinal. In addition, RXR-alpha effects trans-activation in mammalian cells exposed to a number of synthetic retinoids. The dose-response of RXR-alpha in CV-1 monkey kidney cells exposed to retinoic acid differs significantly from the dose response of human RAR-alpha exposed to the same conditions. See commonly owned, copending United States Patent Application Ser. No. 07/478,071, filed Feb. 9, 1990, now abandoned in favor of continuation-in-part U.S. Ser. No. 07/933,453, filed Aug. 21, 1992, now pending, which is incorporated herein by reference in its entirety.

The identification of yet other related receptors, especially from non-mammalian sources, would be of particular interest. Such discoveries would provide a great deal of information on the development of regulatory systems in the animal kingdom, and the potential to exert selective control over the proliferation of various pest species.

Other information helpful in the understanding and practice of the present invention can be found in commonly assigned, co-pending United States Patent Application Ser. Nos. 108,471, filed Oct. 20, 1987, issued Dec. 10, 1991, as U.S Pat. No. 5,071,773; 276,536, filed Nov. 30, 1988, issued Jan. 1, 1991 as U.S. Pat. No. 4,981,784; 325,240, filed Mar. 17, 1989, now abandoned; 370,407, filed Jun. 22, 1989, issued Nov. 9, 1993 as U.S. Pat. No. 5,260,432; and 438,757, filed Nov. 16, 1989, issued Feb. 25, 1992 as U.S. Pat. No. 5,091,518, all of which are incorporated herein by reference in their entirety.

SUMMARY OF THE INVENTION

We have discovered novel insect receptors which have a substantial degree of similarity with respect to mammalian receptors which are activated to modulate transcription of certain genes when exposed to a retinoid, such as retinoic acid, retinol, retinal, retinyl acetate, or retinyl palmitate. The novel insect receptors of the present invention differ significantly from the known RAR-alpha, beta and gamma receptors in primary sequence but share significant homology with mammalian RXR-alpha.

A receptor according to the present invention, XR2C, obtained from Drosophila melanogaster, has been mapped to the Drosophila ultraspiracle locus, a locus known to be required both maternally and zygotically for pattern forma-

3 tion. Thus, compounds which interfere with, or otherwise alter, trans-activation by the receptors of the invention would be expected to be insecticidal.

The invention provides isolated DNAs encoding novel insect receptors, including expression vectors for expression of these receptors in cells, cells containing such expression vectors, cells co-transformed with such expression vectors and with reporter vectors to monitor the ability of invention receptors to modulate transcription, when the cells are exposed to agonists or antagonists for such receptors. The invention further provides methods of using such co-transformed cells in (1) assaying for compounds capable of activating invention receptors, and (2) screening for compounds which are antagonists for invention receptors. Such antagonists are likely to be toxic or lethal to insects.

The invention also provides DNA and RNA probes for identifying DNAs encoding novel, related retinoid-like receptors, and particularly insect retinoid-like receptors (i.e., receptors of the same class as human RXR-alpha).

The invention also provides a method for making the receptors of the invention by expressing DNAs which encode the receptors in suitable host cells. These recombinantly-produced receptors are useful for assessing the ability of receptor agonists or antagonists to bind to invention receptor.

Animal cells, and especially insect cells, in which invention receptors are expressed, can be employed, as more fully taught in the examples, in assaying for the presence of ligands for invention receptor(s).

As indicated above, animal cells, and especially insect cells, of the invention can also be employed to screen compounds of potential value as insecticides.

DETAILED DESCRIPTION OF THE INVENTION

The invention concerns novel isolated polypeptides, which are characterized as having a DNA binding domain of about 66 (i.e., 64–68) amino acids with 10 Cys residues, more than about 75 % amino acid identity with the DNA binding domain of hRXR-alpha, less than about 60 % amino acid identity with the DNA binding domain of hGR, and less than about 60 % amino acid identity in comparison with the DNA binding domain of hRAR-alpha, wherein said polypeptide is structurally and functionally related to the steroid/thyroid superfamily of receptors.

The invention also concerns isolated DNAs encoding polypeptides as described above. Further, the invention encompasses expression vectors operative in animal cells (preferably insect cells) to make proteins encoded by DNAs of the invention.

As employed herein, the term "isolated" refers to polynucleic acids and polypeptides which have been removed from their natural environment. For example, the term "isolated" refers to polynucleic acids which are devoid of some or all of the species with which they are naturally associated in nature. Such materials can be obtained in a variety of ways, such as, for example, by fractionation of cells, by fractionation of cell products, by chemical synthesis, and the like. Similarly, the term "isolated" refers to polypeptides which are devoid of some or all of the species with which they are naturally associated in nature. Such polypeptides are obtained, for example, by recombinant expression of DNA encoding such polypeptides.

Further, the invention provides an animal cell (preferably an insect cell) in culture which is transformed with an expression vector, which is operative in the cell to make invention polypeptide, by expression of the above-described DNA.

Animal cells contemplated by the present invention include cells co-transformed with a reporter vector which comprises (a) an operative promoter, (b) a hormone response element, and (c) DNA encoding a reporter protein, wherein said reporter protein-encoding DNA is operatively linked to said promoter for transcription therefrom and wherein said hormone response element is operatively linked to said promoter for transcription therefrom upon binding of receptor protein at said response element.

The invention also entails a method of testing a compound for its ability to promote the transcription-activating effects of receptor polypeptides of the present invention (as described above), which method comprises:

(A) adding a first concentration of said compound to a first culture of animal (preferably insect) cells, which are co-transformed with
  (i) an expression vector operative to make said receptor polypeptide, and
  (ii) a test vector, which comprises
    (a) an operative promoter,
    (b) a hormone response element, and
    (c) DNA encoding a reporter protein,
  wherein said reporter protein-encoding DNA is operatively linked to said promoter for transcription therefrom, and wherein said response element is operatively linked to said promoter for promoting transcription therefrom upon binding of said response element by said receptor polypeptide, and (B) comparing the rate of production of said reporter protein after addition of a first concentration of the compound to said first culture with the rate of production of said reporter protein in a control culture, where the compound is added at a second concentration that is signficantly (i.e., measurably) different from said first concentration. Preferably, in this method of the invention, the first culture and the control culture are subcultures of a common culture, and the second concentration is 0.

The invention further entails a method of testing a first compound for its ability to affect the transcription-activating properties of a second compound on receptor polypeptides of the invention, said method comprising:

(A) adding said first and second compounds, at a first ratio of concentrations, to a first culture of animal cells and adding said first and second compounds, at a second ratio of concentrations, significantly different from said first ratio, to a second culture of animal cells, said animal cells in said cultures being substantially the same and being co-transformed with:
  (i) an expression vector operative to make said receptor polypeptide, and (ii) a test vector, which comprises:
 (a) an operable promoter,
 (b) a hormone response element, and
 (c) DNA encoding a reporter protein,
wherein said reporter protein-encoding DNA segment is operatively linked to said promoter for transcription therefrom and wherein said response element is operatively linked to said promoter for transcription therefrom upon binding of receptor polypeptide at the response element, and (B) comparing the rate of production of said reporter protein in said first culture with the rate of production of reporter protein in said second culture, provided that the concentration of second compound in both cultures is such that, if said first compound were not present in said cultures, the concentrations of second compound would be sufficient to promote trans-activation by said receptor protein.

Preferably, the various cultures, in which different concentration ratios of first and second compound are compared in accordance with the above-described method, are all subcultures of a common culture, and all have the same concentration of second compound.

Further, the invention encompasses various probes, which can be used to identify genes encoding receptors related to those with which the present invention is concerned. In this regard, particular reference is made to Example 4 below. More particularly, the invention provides a DNA (or RNA derived therefrom) which DNA or RNA is labelled for detection and comprises a segment of at least 20 bases in length which has the same sequence as (i) a segment of the same length selected from bases 1–2271, inclusive, of the DNA set forth in SEQ ID No:1, (ii) a segment of RNA derived from the sequence of (i), or (iii) the complement of any one of said segments.

The invention also encompasses a method of making invention polypeptide which method comprises culturing cells which are transformed with an expression vector operable in said cells to express DNA encoding said polypeptide. In this method of the invention, *E. coli* is the preferred bacterial species. Any of a number of bacterial expression vectors are well known to those skilled in the art that could be employed in the method of the invention. Among these are the prokaryotic expression vectors pNH8A, pNH16A and pNH18A available from Stratagene, La Jolla, Calif. USA. Similarly, those of skill in the art recognize that yeast, mammalian, or viral expression vectors (and suitable hosts therefor) can also be employed for such expression.

Further information on the invention is provided in the following non-limiting examples and description of a deposit.

EXAMPLE 1

The KpnI/SacI restriction fragment (503 bp) including the DNA-binding domain of hRAR-alpha-encoding DNA (Giguere et al., Nature 330:624 (1987); commonly assigned United States Patent Application Ser. No. 276,536, filed Nov. 30, 1988, issued Jan. 1, 1991 as U.S. Pat. No. 5,071,773; European Patent Application Publication No. 0 325 849, all incorporated herein by reference) was nick-translated and used to probe a Southern blot of EcoRI-digested, genomic DNA of *Drosophila melanogaster* to identify potential homologs of vertebrate steroid hormone receptors. Under conditions of reduced hybridization stringency, six distinct EcoRI bands, ranging in size from 2 kilobases ("kb") to 12 kb, were detected (see Oro et al., Nature 336:493 (1988)). Using the same probe and reduced stringency conditions, screening of a *D. melanogaster* genomic library in lambda-gt11 resulted in the isolation of three classes of inserts, based on cross-hybridization under high stringency conditions. Representatives of each class were hybridized to larval salivary gland polytene chromosomes to identify their cytogenetic location. One class of inserts mapped to 2C9 on the *D. melanogaster* first chromosome and was labelled XR2C. A portion of the XR2C genomic insert hybridizing most strongly to the fragment of the hRAR-alpha-encoding DNA probe was designated pHX3.5, subcloned and sequenced. The deduced amino acid sequence of one of the reading frames in pHX3.5 had the structural features of asteroid receptor DNA binding domain.

pHX3.5 was used as a probe to screen a total third instar larval imaginal disc cDNA library from D. melanogaster in the EcoRI site of BluescriptR phagemid SK(+) (Stratagene, La Jolla, Calif., USA). Six cDNA clones were identified by this procedure. The complete nucleotide sequence of the longest, designated pXR2C8, except for the overhanging EcoRI ends, is presented in SEQ ID No:1, along with the deduced amino acid sequence of the 513 amino-acid XR2C encoded by the segment of pXR2C8 from nucleotides 163–1701.

The gene for XR2C has been mapped to the ultraspiracle locus of *D. melanogaster*, indicating that function of the XR2C receptor is essential for normal development and that interruption of the function early in development would be lethal.

EXAMPLE 2

Figure 1:
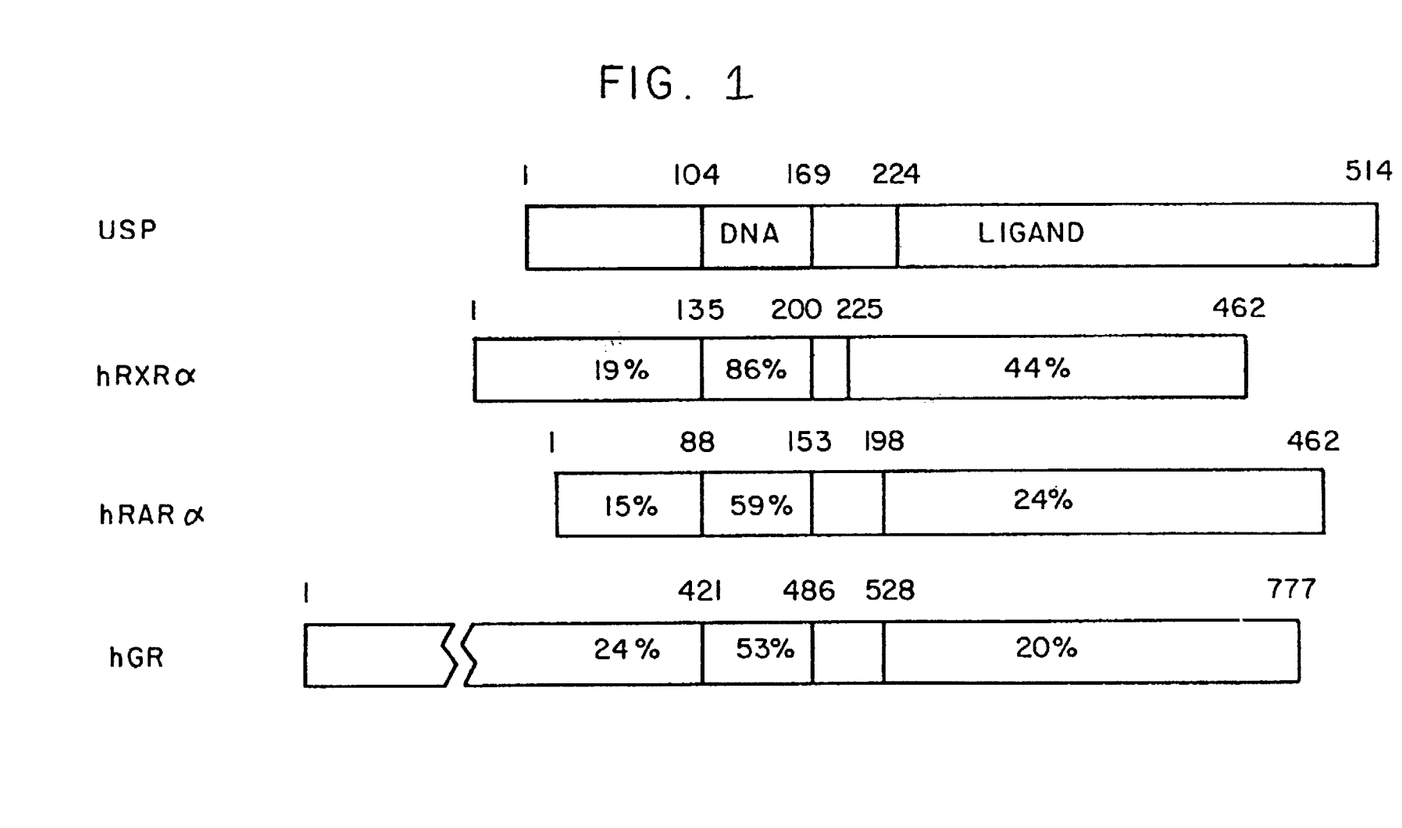
FIG. 1 shows the extent of amino acid identity (i.e., "homology") between the DNA binding domain ("DNA") and ligand binding domain ("LIGAND") of XR2C (designated in the Figure as "USP" because it is the product of the ultraspiracle locus of *D. melanogaster*) (taken to have 100% identity in both domains) and the corresponding domains of human RXR-alpha, human retinoic acid receptor-alpha (hRAR-alpha), and human glucocorticoid receptor (hGR). The numbers outside the boxes in the Figure are the numbers, in the primary sequences of the proteins, of the amino acids defining the two domains and the amino- and carboxy-termini.

Amino acid sequences of XR2C, hRXR-alpha (commonly owned United States Patent Application Ser. No. 478,071, filed Feb. 9, 1990, now abandoned in favor of continuation-in-part U.S. Ser. No. 07/933,453, filed Aug. 21, 1992, now abandoned in favor of file-wrapper continuation application U.S. Ser. No. 08/336,408, filed Nov. 8, 1994, incorporated herein by reference), hRAR-alpha (human retinoic acid receptor-alpha) (Giguere et al., Nature 330:624 (1987); commonly asigned United States Patent Application Ser. No. 276,536, filed Nov. 30, 1988, issued Jan. 1, 1991 as United States Pat. No. 5,071,773; European Patent Application Publication No. 0 325 849, all incorporated herein by reference); and hGR (human glucocorticoid receptor) (Hollenberg et al., Nature 318:635 (1985), commonly assigned United States Patent Application Ser. No. 07/108, 471, filed Oct. 20, 1987, issued Dec. 10, 1991, as U.S Pat. No. 5,071,773; PCT International Publication No. WO 88/03168, all incorporated herein by reference), were aligned using the University of Wisconsin Genetics Computer Group program "Bestfit" (Devereux et al., supra). Regions of significant similarity between XR2C and the other receptors, i.e., the 66–68 amino acid DNA binding domains and the ligand-binding domains) are presented schematically in FIG. 1 as percent amino acid identity. From FIG. 1, it is clear that XR2C is more closely related to human RXR-alpha than to the other two receptors.

The DNA binding domain of XR2C is 66 amino acids in length (amino acids 104–169 of XR2C) and includes 10 cysteines.

EXAMPLE 3

*Drosophila melanogaster* Schneider line 2 ("S2") cells (Schneider, Embryol. Exp. Morphol. 27:353 (1972), which are widely available and readily available to the skilled, are seeded at $2 \times 10^6$ per 35 mm$^2$ culture dish and maintained in Schneider medium (GIBCO/Life Technologies, Inc., Grand Island, N.Y., USA) supplemented with penicillin, streptomycin and 12% heat-inactivated fetal bovine serum (Irvine Scientific, Santa Ana, Calif., USA). The cells are transiently cotransfected with 10 µg/dish plasmid DNA by calcium phosphate precipitation (Krasnow et al., Cell 57, 1031 (1989): 4.5 µg/dish receptor expression construct or control construct (producing no XR2C); 0.5 µg/dish reporter plasmid or control reporter plasmid; 0.5 µg/dish reference plasmid; and 4.5 µg inert plasmid DNA.

In the receptor expression construct, i.e., receptor expression vector (4.5 µg/dish), XR2C is constitutively expressed in the S2 cells under the control of the Drosophila actin 5C promoter (Thummel et al., Gene 74:445 (1988)) driving transcription of the EcoRI-site-bounded insert of pXR2C8. In the control vector (also 4.5 µg/ml), the EcoRI-site-bounded insert from pXR2C8 is inserted in the reverse orientation (i.e., non-coding or non-sense-coding) orientation in comparison with the orientation in the receptor expression construct. The receptor expression construct is made by first inserting at the unique BamHI site of A5C a linker of sequence:

5'-GATCCGATATCCATATGGAATTCGGTACCA (SEQ ID NO:3)

and then inserting, in the XR2C-coding orientation, into the modified A5C at the EcoRI site of the linker, the EcoRI-site-bounded insert of pXR2C8.

The reporter plasmid, i.e., a test vector, ADH-TRE$_p$-CAT (at 0.5 µg/dish) contains the palindromic thyroid hormone response element TREp (having the sequence 5'-AGGTCATGACCT; SEQ ID NO:4; see Glass et al. Cell 54:313 (1988); Thompson and Evans, Proc. Natl. Acad. Sci. (USA) 86:3494 (1989), inserted into position -33 (with respect to the transcription start site) of a pD33-ADH-CAT background (Krasnow et al., Cell 57:1031 (1989)). pD33-ADH-CAT is a plasmid with the distal promoter of the *Drosophila melanogaster* alcohol dehydrogenase gene linked operably for transcription to the bacterial (*E. coli*) chloramphenicol acetyltransferase ("CAT") gene, a gene for the indicator protein CAT. ADH-TREp-CAT was made by inserting the oligonucleotide of sequence (SEQ ID NO:5):

5'-CTAGAGGTCATGACCT
TCCAGTACTGGAGATC-5' into the XbaI site at the aformentioned position -33 in pD33-ADH-CAT. pD33-ADH-CAT, without TREp, served as a control reporter plasmid.

A reference plasmid containing the beta-galactosidase transcription unit driven by the actin 5C promoter also is transfected (0.5 µg/dish) along with pGEM DNA (4.5 µg/dish) (Promega, Madison, Wis.) to make up the final DNA concentration to 10 µg/dish. The reference plasmid is made by inserting a BamHI-site bounded, beta-galactosidase-encoding segment into the unique BamHI site of A5C. The purpose of the reference plasmid was to normalize results for transfection efficiency.

24 h post-transfection, retinoic acid is added to the cultures. The retinoic acid is dissolved in ethanol and the resulting solution is added to 0.1% v/v of culture medium. Initial concentration of the retinoic acid in the culture media is $10^{-6}$M, $5 \times 10^{-7}$M or $10^{-8}$M.

In control runs, ethanol, at 0.1% v/v in the medium, is used in place of a solution of retinoid.

Cultures are maintained in the dark for 36 hr after addition of retinoic acid and then harvested. All other parts of the experiments are carried out in subdued light.

Cell lysates are centrifuged. Supernatants are assayed for beta-galactosidase, following Herbomel et al., Cell 39:653–662 (1984), and units/ml of beta-galactosidase activity is calculated. CAT assays (normalized to beta-gal activity) of supernatants are incubated for 75 unit-hours ("units" referring to units of beta-gal actvity), as described by Gorman et al., Mol. Cell. Biol. 2:1044 (1982), usually 150 units for 30 minutes.

No XR2C-dependent activation of CAT expression is noted in any experiment in which control reporter is used in place of ADH-TREp-CAT. Similarly, essentially no activation is observed for runs where control plasmid is used in place of receptor expression plasmid.

Results can be expressed in terms of fold-induction of CAT activity in retinoic acid-treated cells in comparison with untreated (i.e., only ethanol-treated) cells.

The level of expression of CAT can be monitored to observe if there is a significant increase or decrease between the test cells exposed to an initial concentration of retinoic acid of 10–6M (higher level of expression) and those exposed to an initial concentration of retinoic acid of $5 \times 10^{-7}$M. Similarly, the level of expression with test cells exposed to an initial concentration of retinoic acid of $5-10^{-7}$M can be monitored to observe if there is a significant increase or decrease in CAT expression, relative to cells exposed to an initial concentration of retinoic acid of $10^{-8}$M.

EXAMPLE 4

To analyze insect DNA for homologs of XR2C, two genomic DNA Southern blots are prepared in parallel with identical DNA samples from insects of a particular species. The blots are hybridized at high or low stringency with a ~1300 bp [$^{32}$P]-labelled fragment of pXR2C8 which includes the coding portions of the DNA and ligand binding domains (nucleotides 472–1701, see SEQ ID NO:1) or an approx. 450 bp $^{32}$P-labelled PstI-BamHI fragment (approx. nucleotide 419—approx. nucleotide 774) including the DNA encoding the DNA-binding domain (nucleotides 472–669, see SEQ ID NO:1).

Blots are hybridized at 42° C. in a low stringency buffer (35 % formamide, 1×Denhardt's, 5×SSPE (1×SSPE =0.15M NaCl, 10 mM Na$_2$HPO$_4$, 1 mM EDTA), 0.1% SDS, 10% dextran sulfate, 100 mg/ml denatured salmon sperm DNA and 106 cpm of $^{32}$P-labelled probe) for low stringency hybridization or at high stringency in the same buffer modified by addition of formamide to 50%. Low stringency blots are washed twice at room temperature and twice at 50° C. in 2×SSC, 0.1% SDS. The high stringency blot is washed twice at room temperature in 2×SSC, 0.1% SDS and twice at 65° C. in 0.5×SSC, 0.1% SDS.

DEPOSIT

On Nov. 10, 1989, viable cultures of *E. coli* DH5 transformed with pXR2C8 were deposited under the terms of the Budapest Treaty on the International Recognition of the Deposit of Microorganisms for the Purposes of Patent Procedure at the American Type Culture Collection, Rockville, Md., USA ("ATCC"). The accession number assigned to this deposit is ATCC 68171.

Samples of *E. coli* DH5(pXR2C8) will be publicly available from the ATCC without restriction, except as provided in 37 CFR 1.801 et seq., at the latest on the date an United States Patent first issues on this application or a continuing application thereof. Otherwise, in accordance with the Budapest Treaty and the regulations promulgated thereunder, samples will be available from the ATCC to all persons legally entitled to receive them under the law and regulations of any country or international organization in which an application, claiming priority of this application, is filed or in which a patent based on any such application is granted.

Although the invention has been described herein with some specificity, those of skill in the art will recognize modifications and variations of what has been described that fall within the spirit of the invention. These modifications and variations are also intended to be within the scope of the invention as described and claimed.

What is claimed:

1. An isolated DNA encoding an insect retinoid-like receptor polypeptide which is structurally and functionally related to the steroid/thyroid superfamily of receptors wherein said polypeptide is characterized by having:

an amino-terminal domain of about 104 amino acids, wherein said amino terminal domain has:
  (a) about 19% amino acid identity with the amino-terminal domain of hRXR-alpha,
  (b) about 24% amino acid identity with the amino-terminal domain of hGR, and
  (c) about 15% amino acid identity with the amino-terminal domain of hRARα;

a DNA binding domain of about 66 amino acids with 10 Cys residues, wherein said DNA binding domain has:
  (a) more than about 75% amino acid identity with the DNA binding domain of hRXR-alpha,
  (b) less than about 60% amino acid identity with the DNA binding domain of hGR, and
  (c) less than about 60% amino acid identity with the DNA binding domain of hRARα; and a ligand-binding domain of about 290 amino acids, wherein said ligand-binding domain has:
  (a) about 44% amino acid identity with the ligand-binding domain of hRXR-alpha,
  (b) about 20% amino acid identity with the ligand-binding domain of hGR, and
  (c) about 24% amino acid identity with the ligand-binding domain of hRARα.

2. DNA according to claim 1 wherein the DNA binding domain of said polypeptide has the same sequence as that of amino acids 104–169 shown in SEQ ID NO:1.

3. DNA according to claim 2 wherein said DNA encodes a polypeptide having the same sequence as that of amino acids 1–513 shown in SEQ ID NO:1.

4. DNA according to claim 3 wherein said DNA comprises a segment with the same nucleotide sequence as nucleotides 163–1704 shown in SEQ ID NO:1.

5. DNA according to claim 4 which is pXR2C8.

6. An expression vector containing DNA according to claim 1, wherein said DNA is operative in a cell in culture to express said polypeptide.

7. An expression vector according to claim 6 wherein transcription of said DNA is controlled by the Drosophila melanogaster actin 5C promoter.

8. An insect cell which is transformed with an expression vector according to claim 6.

9. A cell according to claim 8 which is a Drosophila melanogaster Schneider line 2 cell.

10. A cell according to claim 8, wherein said cell is further transformed with a reporter vector which comprises:
  (a) an operative promoter,
  (b) a hormone response element, and
  (c) DNA encoding a reporter protein, wherein said reporter protein-encoding DNA is operatively linked to said promoter for transcription of said DNA, and
wherein said hormone response element is operatively linked to said promoter for activation thereof.

11. A cell according to claim 10 wherein:

said promoter is the distal promoter of the Drosophila melanogaster alcohol dehydrogenase gene, the hormone response element is selected from TREp or beta-RARE, and the reporter protein is chloramphenicol acetyltransferase.

12. A cell according to claim 11 wherein the reporter vector is the plasmid ADH-TREp-CAT.

13. DNA or RNA derived therefrom, wherein said DNA or RNA is labelled for detection and comprises a segment of at least 20 bases in length, and wherein said DNA which has the same sequence as either:
  (i) a segment of the same length selected from bases 1–2271, inclusive, of the DNA illustrated in SEQ ID NO:1,
  (ii) RNA derived from the DNA of (i), or
  (iii) the complement of any one of said segments.

\* \* \* \* \*